US012590010B2

(12) United States Patent
Ejiri et al.

(10) Patent No.: US 12,590,010 B2
(45) Date of Patent: Mar. 31, 2026

(54) TITANIUM OXIDE POWDER AND METHOD FOR MANUFACTURING SAME

(71) Applicant: Tayca Corporation, Osaka (JP)

(72) Inventors: Kazumasa Ejiri, Osaki (JP); Kazuya Shibata, Osaka (JP); Yuka Hashizume, Osaka (JP)

(73) Assignee: TAYCA CORPORATION, Osaka (JP)

( * ) Notice: Subject to any disclaimer, the term of this patent is extended or adjusted under 35 U.S.C. 154(b) by 864 days.

(21) Appl. No.: 17/610,747

(22) PCT Filed: May 13, 2020

(86) PCT No.: PCT/JP2020/019093

§ 371 (c)(1),
(2) Date: Nov. 12, 2021

(87) PCT Pub. No.: WO2020/230812

PCT Pub. Date: Nov. 19, 2020

(65) Prior Publication Data

US 2022/0064016 A1 Mar. 3, 2022

(30) Foreign Application Priority Data

May 14, 2019 (JP) ................................. 2019-091248

(51) Int. Cl.
*C01G 23/08* (2006.01)
*A61K 8/29* (2006.01)
*C01G 23/053* (2006.01)

(52) U.S. Cl.
CPC ................ *C01G 23/08* (2013.01); *A61K 8/29* (2013.01); *C01G 23/0532* (2013.01);
(Continued)

(58) Field of Classification Search
CPC ... C01G 23/047; C01G 23/08; C01G 23/0532
See application file for complete search history.

(56) References Cited

U.S. PATENT DOCUMENTS 6,534,044 B1 * 3/2003 Wada ...................... C09C 1/043
424/59
2007/0161504 A1 7/2007 Ohno et al.
(Continued)

FOREIGN PATENT DOCUMENTS

JP 2006089343 A 4/2006
JP 2008230950 * 10/2008 .............. B01J 21/06
(Continued)

OTHER PUBLICATIONS

Zhang, et al. "Preparation of long TiO2 nanotubes from ultrafine rutile nanocrystals." Chemistry Letters 31.2 (2002): 226-227 (Year: 2002).*

(Continued)

*Primary Examiner* — Anthony J Zimmer
*Assistant Examiner* — Eric Scott Sherman
(74) *Attorney, Agent, or Firm* — BUCHANAN INGERSOLL & ROONEY PC

(57) ABSTRACT

In producing titanium oxide containing rutile-type crystals by adding hydrochloric acid to an aqueous dispersion of an alkali metal titanate, sulfurous acid, disulfurous acid, sulfuric acid or a salt thereof is added. Thus, there is provided a titanium oxide powder which is doped with bivalent sulfur atoms ($S^{2-}$) and in which a ratio ($I_A/I_R$) of a peak intensity ($I_A$) of anatase-type crystals to a peak intensity ($I_R$) of rutile-type crystals as measured by X-ray diffractometry is 0.1 or less. Moreover, a cosmetic is provided by dispersing the titanium oxide powder in a dispersion medium. Thus, bluish color derived from Rayleigh scattering is negated, providing a dispersion, particularly a cosmetic, with excellent transparency and color tone.

24 Claims, 4 Drawing Sheets

(52) U.S. Cl.

CPC ...... *C01P 2002/74* (2013.01); *C01P 2004/64* (2013.01); *C01P 2006/12* (2013.01)

(56) References Cited

U.S. PATENT DOCUMENTS

| | | |
|---|---|---|
| 2010/0189666 A1 | 7/2010 | Nakamura et al. |
| 2013/0115308 A1 | 5/2013 | Gannon et al. |
| 2014/0112965 A1 | 4/2014 | Nakamura et al. |
| 2015/0329723 A1* | 11/2015 | Wachi ...................... C09D 7/61 106/31.9 |
| 2018/0261838 A1 | 9/2018 | Capiglia et al. |

FOREIGN PATENT DOCUMENTS

| | | |
|---|---|---|
| JP | 2010173863 A | 8/2010 |
| JP | 2011001199 A | 1/2011 |
| JP | 2011120998 A | 6/2011 |
| JP | 2014084251 A | 5/2014 |
| JP | 2016108267 A | 6/2016 |
| JP | 2018535177 A | 11/2018 |
| WO | 2005087372 A1 | 9/2005 |

OTHER PUBLICATIONS

Liu, et al. "(Sulfur, Nitrogen)-Codoped RutileTitanium Dioxide as a Visible Light Activated Photocatalyst." Journal of the American Ceramic Society 87.8 (2004): 1582-1584 (Year: 2004).*

Lin, et al. "TiS2 transformation into S-doped and N-doped TiO2 with visible-light catalytic activity." Applied Surface Science 359 (2015): 1-6 (Year: 2015).*

Office Action (Notification of the First Office Action) issued on Feb. 25, 2023, by the China National Intellectual Property Administration in corresponding Chinese Patent Application No. 202080048719. 6, and a partial English translation of the Office Action. (11 pages).

Umebayashi, T. et al., "Sulfur-doping of rutile-titanium dioxide by ion implantation: Photocurrent spectroscopy and first-principles band calculation studies", Journal of Applied Physics, May 1, 2003, vol. 93, No. 9, pp. 5156-5160.

Yang, C. et al., "Core-Shell Nanostructured 'Black' Rutile Titania as Excellent Catalyst for Hydrogen Production Enhanced by Sulfur Doping", Journal of American Chemical Society, 2013, vol. 135, No. 47, pp. 17831-17838.

Ohno, T., "Preparation of visible light active S-doped TiO2 photocatalysts and their photocatalytic activities", Water Science and Technology, 2004, vol. 49, No. 4, pp. 159-163, IWA Publishing. (5 pages).

Ohno, Teruhisa, et al., "Preparation of S-doped TiO2 photocatalysts and their photocatalytic activities under visible light", Science Direct, Applied Catalysis A:General, 2004, vol. 265, pp. 115-121, Elsevier B.V. (7 pages).

Umebayashi T., et al., "Band gap narrowing of titanium dioxide by sulfur doping", Applied Physics Letters, Jul. 15, 2002, vol. 81, No. 3, pp. 454-456, American Institute of Physics. (3 pages).

Extended European Search Report dated Dec. 15, 2022, issued by the European Patent Office in corresponding European Application No. 20805770.3. (8 pages).

JP2006-089343 A English machine translation (20 pgs).

* cited by examiner

[FIG. 1]
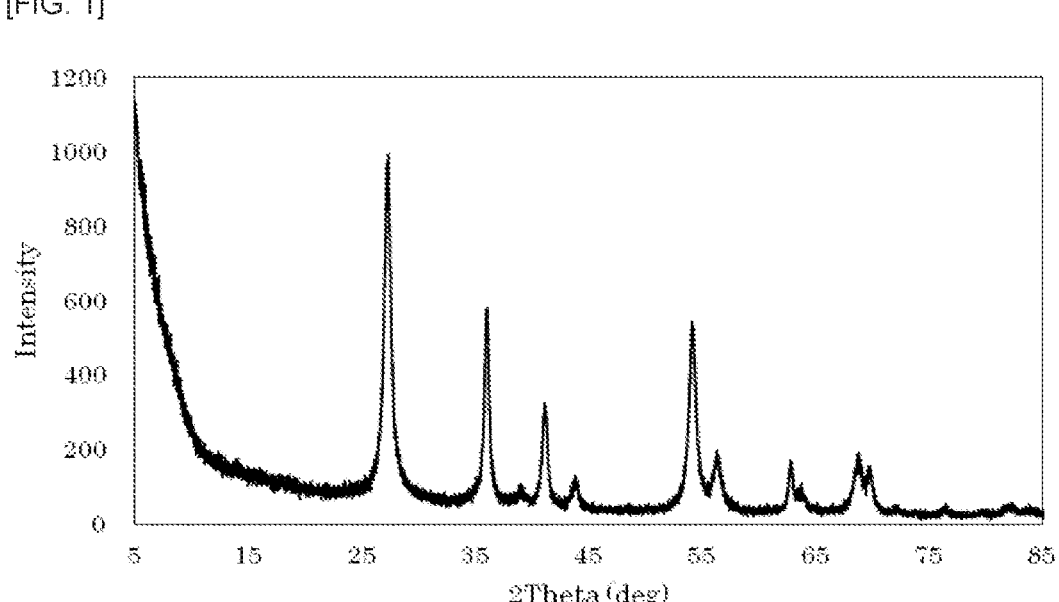
[FIG. 2]
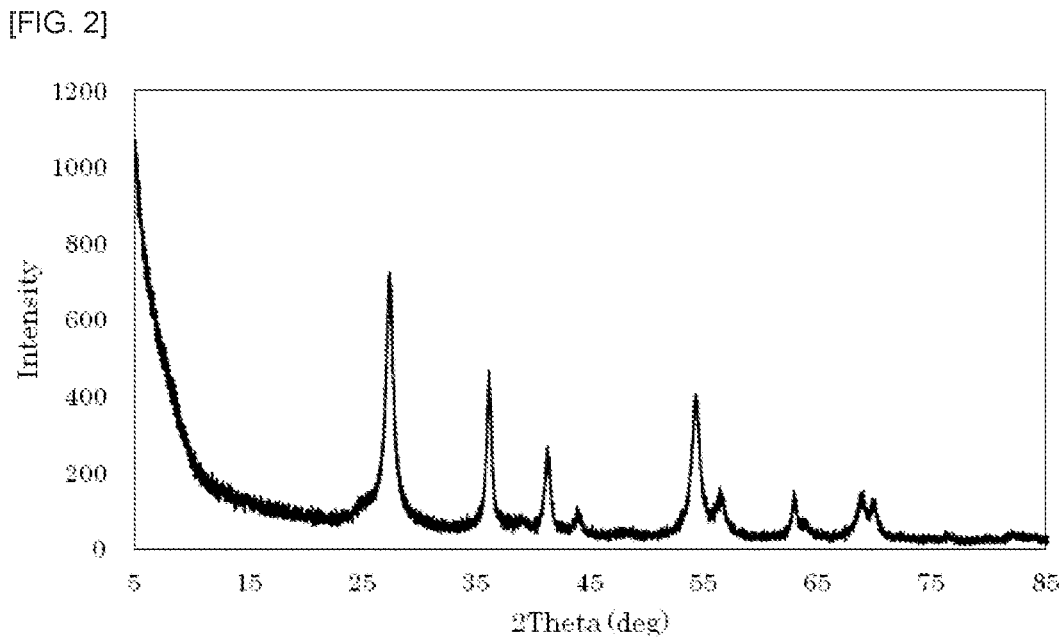

[FIG. 3]
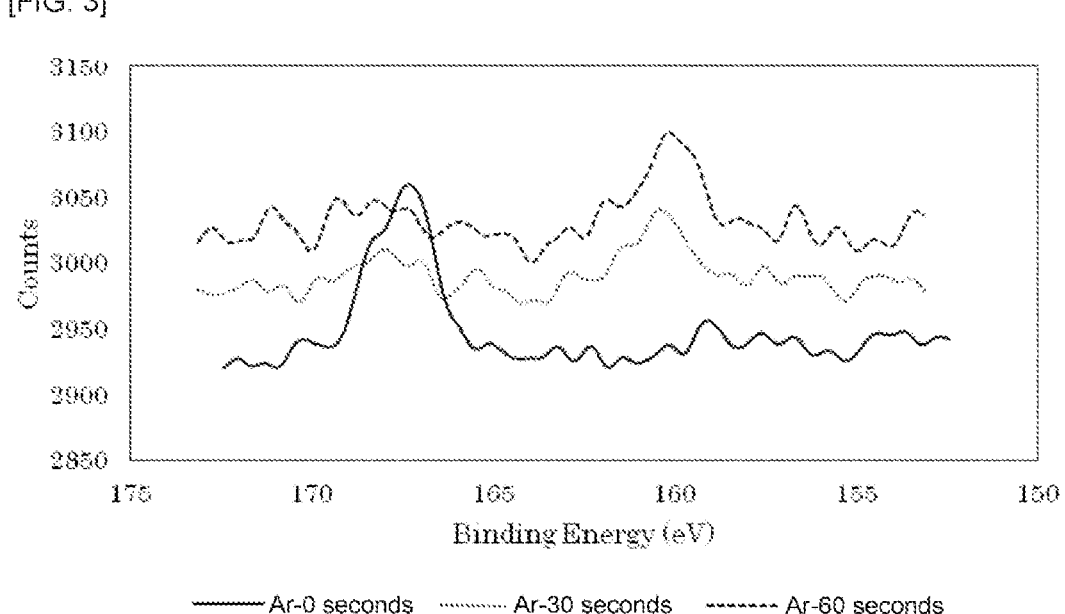
[FIG. 4]
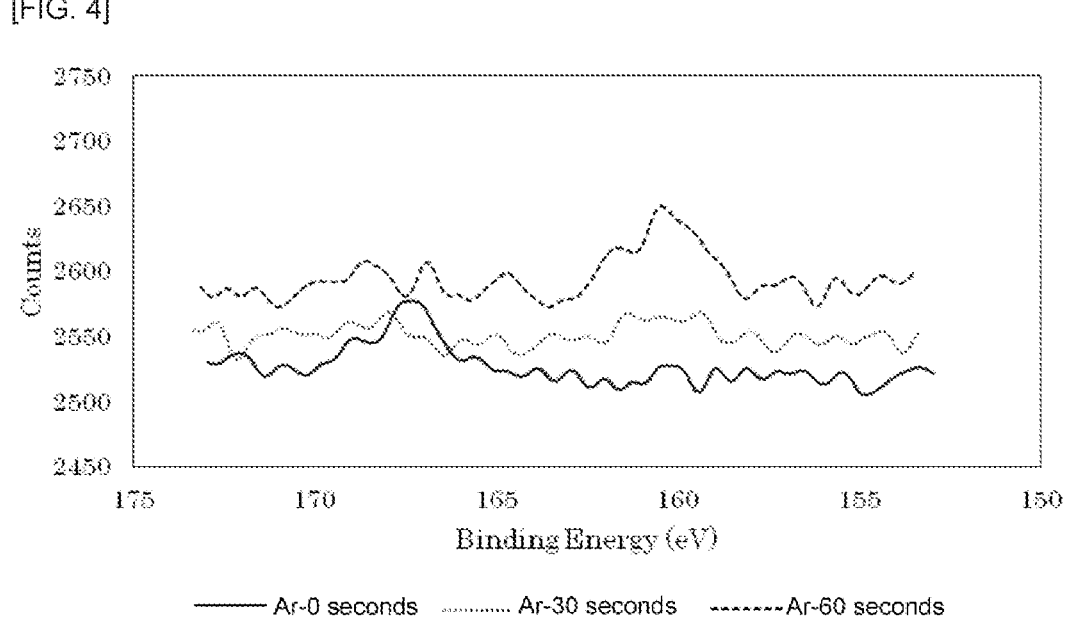

[FIG. 5]
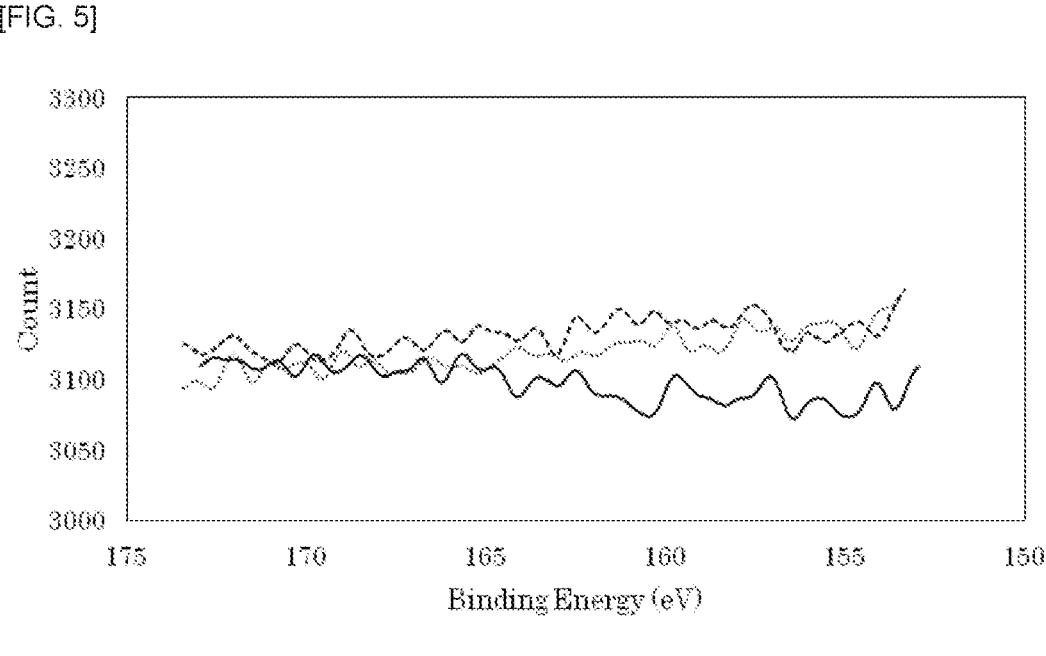
Ar-0 seconds       Ar-30 seconds       Ar-60 seconds
[FIG. 6]
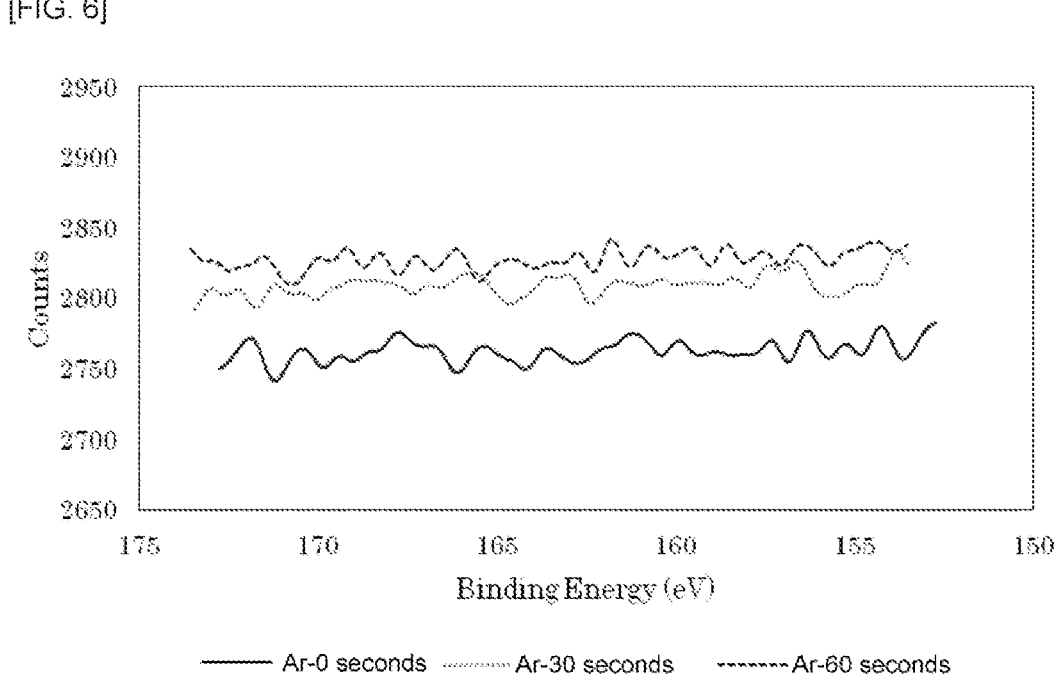
Ar-0 seconds       Ar-30 seconds       Ar-60 seconds

[FIG. 7]
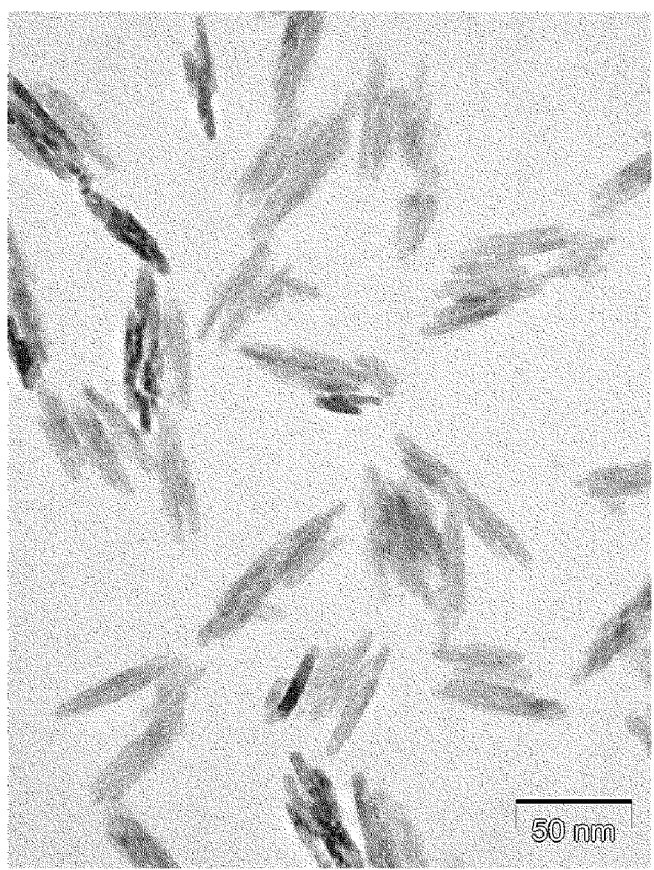
[FIG. 8]
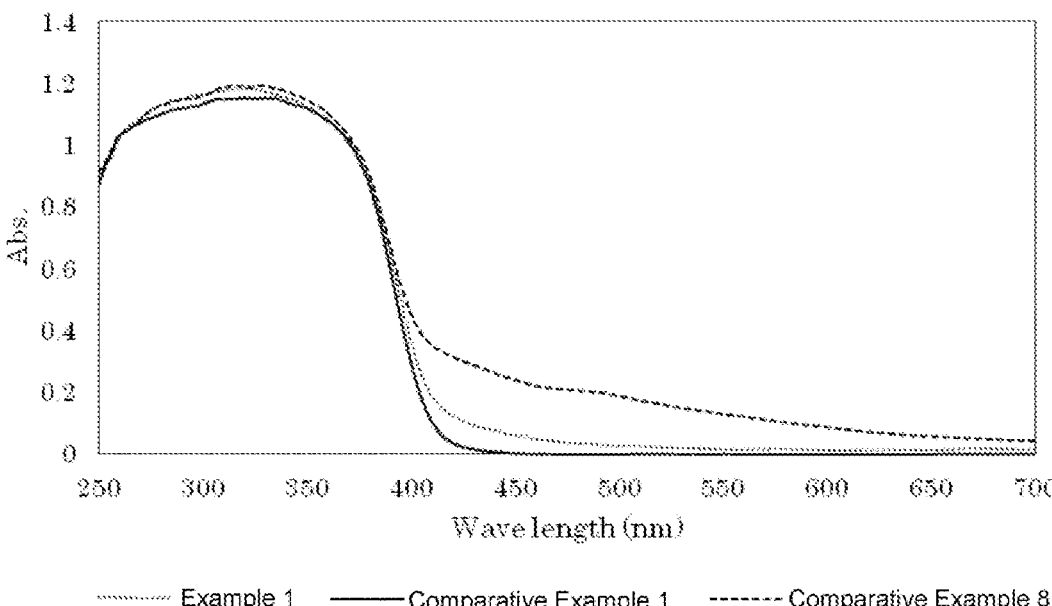
·············· Example 1 ——— Comparative Example 1 ------- Comparative Example 8

TITANIUM OXIDE POWDER AND METHOD FOR MANUFACTURING SAME

TECHNICAL FIELD

The present invention relates to a titanium oxide powder, its use and a production method therefor.

BACKGROUND ART

Sunscreen cosmetics are widely used because sunburn caused by ultraviolet rays has an adverse effect on the skin. Moreover, not only sunscreen cosmetics but also make-up cosmetics have been often required to have an ultraviolet shielding effect. For the purpose of that, cosmetics containing inorganic particles such as titanium oxide and zinc oxide and/or organic ultraviolet absorbers have been developed. Among these, titanium oxide has been widely used because it has higher ultraviolet shielding effect and is less likely to cause skin troubles caused by an organic ultraviolet absorber. In particular, titanium oxide fine particles having a particle size of several tens of nm or less are excellent in visible light transmission because their size is smaller than the wavelength of light, and in cosmetics containing such particles, whiteness derived from titanium oxide is reduced and transparency during use is excellent (see Patent Reference Nos. 1 to 3).

However, the finer and more dispersed it is for improving transparency, the more susceptible to Rayleigh scattering it is. Intensity of Rayleigh scattering is stronger as the particles become smaller, and blue light is more likely to be scattered than red light, so that a bluish color is felt when a cosmetic containing fine particles of titanium oxide is applied to the skin. The bluish white color is undesirable as a cosmetic because the skin color looks unhealthy.

To address the problem, there is an approach that a small amount of iron oxide ($Fe_2O_3$) is added to negate the bluish color. However, since iron oxide shows not only yellow which is the complementary color of blue, but also red, it is inevitable that the cosmetic becomes dull in hue. Thus, a better approach has been desired.

Non-patent Reference No. 1 describes a sulfur-doped titanium oxide photocatalyst, wherein the titanium oxide is synthesized using thiourea as a sulfur source. It has been confirmed by ESCA that titanium oxide particles containing only anatase-type crystals at the beginning of the synthesis are doped with bivalent sulfur atoms ($S^{2-}$). When it was fired at 500° C., the crystal morphology remained as anatase-type crystals and bivalent sulfur atoms ($S^{2-}$) disappeared, and instead, titanium oxide particles doped with tetravalent sulfur atoms ($S^{4+}$) were obtained. By further firing it at 600 to 700° C., titanium oxide particles containing rutile-type crystals and doped with tetravalent sulfur atoms ($S^{4+}$) were obtained. The document describes that the particles doped with tetravalent sulfur atoms ($S^{4+}$) can absorb visible light and thus are useful as photocatalytic particles responsive to visible light. However, it does not describe titanium oxide particles containing rutile-type crystals as a main component and doped with bivalent sulfur atoms ($S^{2-}$).

Non-patent Reference No. 2 describes that titanium oxide doped with bivalent sulfur atoms ($S^{2-}$) can be obtained by heat-oxidizing titanium sulfide ($TiS_2$). It also describes that doping with bivalent sulfur atoms ($S^{2-}$) allows an absorption edge to be shifted to a longer wavelength side, so that the titanium oxide becomes useful as visible-light responsive photocatalytic particles. The document describes that the titanium oxide was, as an example, heated at 600° C. and most of the crystals contained in the titanium oxide are of an anatase type and only a negligible amount of rutile type crystals are formed. Therefore, Non-patent Reference No. 2 does not describe titanium oxide particles containing rutile-type crystals as a main component and doped with bivalent sulfur atoms ($S^{2-}$). Both Non-patent Reference Nos. 1 and 2 aim to improve visible light responsiveness of a photocatalyst, and do not target titanium oxide particles containing rutile-type crystals having low photocatalytic activity.

Patent Reference No. 4 describes that a mixture of rutile-type titanium oxide and thiourea is fired to give rutile-type titanium oxide doped with carbon atoms as $C^{4+}$ and also doped with sulfur atoms as $S^{4+}$. It describes that the titanium oxide is useful as visible-light responsive photocatalyst particles. However, Patent Reference No. 4 does not describe titanium oxide particles doped with bivalent sulfur atoms ($S^{2-}$).

PRIOR ART REFERENCES

Patent References

Patent Reference No. 1: JP 2010-173863A
Patent Reference No. 2: JP2011-001199A
Patent Reference No. 3: JP 2014-084251A
Patent Reference No. 4: JP 2006-089343A

Non-Patent References

Non-patent Reference No. 1: T. Ohno et al., Applied Catalysis, A: General, 265, (2004), p. 115-121
Non-patent Reference No. 2: T. Umebayashi et al., Applied Physics Letters, vol. 81, no. 3, (2002), p. 454-456

SUMMARY OF THE INVENTION

Problems to be Solved by the Invention

To solve the above problems, an objective of the present invention is to provide a titanium oxide powder containing rutile-type crystals as a main component and doped with bivalent sulfur atoms ($S^{2-}$). Thus, another objective of the present invention is to provide a dispersion, particularly a cosmetic which can negate bluish color derived from Rayleigh scattering and is excellent in transparency and color tone. Another objective of the present invention is to provide a suitable method for producing such titanium oxide particles.

Means for Solving the Problems

The above problems can be solved by providing a titanium oxide powder, wherein the titanium oxide powder is doped with bivalent sulfur atoms ($S^{2-}$) and a ratio ($I_A/I_R$) of a peak intensity ($I_A$) of anatase-type crystals to a peak intensity ($I_R$) of rutile-type crystals as measured by X-ray diffractometry is 0.1 or less.

It is herein preferable that no peaks of anatase-type crystals are observed in the above X-ray diffractometry. It is also preferable that a sulfur content is 500 to 6000 ppm. It is also preferable that particles contained in the above powder have an average short-axis length of 4 to 13 nm and an average aspect ratio of 2 to 7. It is also preferable that a specific surface area is 110 to 300 $m^2/g$. It is also preferable that in an L*a*b* color scale, an L* value is 94 to 99, an a* value is −2 to 1, and a b* value is 2 to 10.

In a preferable embodiment, the surface of particles contained in the above powder is coated with an inorganic or organic compound layer. Herein, preferred is the titanium oxide powder, wherein the surface of the above particles is coated with an inorganic compound layer and the inorganic compound contains at least one element selected from the group consisting of aluminum, magnesium, calcium, silicon, zinc, titanium, zirconium, iron, cerium and tin. Also, preferred is the titanium oxide powder, wherein the surface of the above particles is coated with an organic compound layer and the organic compound is at least one selected from the group consisting of a fatty acid or a salt thereof, a silicone compound, a coupling agent and a fluorine compound.

A preferable embodiment is a dispersion wherein the above titanium oxide powder is dispersed in a dispersion medium. Another preferable embodiment is a cosmetic, a paint or an ink comprising the above titanium oxide powder. Another preferable embodiment is a toner comprising, as an external additive, the above titanium oxide powder.

The above problems can be also solved by providing a method for producing the above titanium oxide powder, comprising an alkalization step of adding an alkali metal hydroxide to an aqueous dispersion of hydrous titanium oxide to provide an alkali metal titanate, an acidification step of adding hydrochloric acid to an aqueous dispersion of the above alkali metal titanate to provide titanium oxide containing rutile-type crystals, and a drying step of drying the above titanium oxide containing rutile-type crystals by heating;

wherein, after the above alkalization step and before the above drying step, sulfurous acid, disulfurous acid, sulfuric acid or a salt thereof is added.

Herein, it is preferable that the amount of sulfurous acid, disulfurous acid, sulfuric acid or a salt thereof added is 0.005 to 0.1 in a mass ratio based on the amount of titanium oxide ($TiO_2$). It is also preferable that the titanium oxide powder obtained by the above production method is coated with an inorganic or organic compound layer.

Effects of the Invention

A titanium oxide powder of the present invention contains rutile-type crystals as a main component and is doped with bivalent sulfur atoms ($S^{2-}$).

Thus, a dispersion, particularly a cosmetic which can negate bluish color derived from Rayleigh scattering and is excellent in transparency and color tone can be provided. According to a production method of the present invention, such a titanium oxide powder can be easily provided.

BRIEF DESCRIPTION OF DRAWINGS

FIG. 1 is an X-ray diffractometry chart for a titanium oxide powder produced in Example 1.

FIG. 2 is an X-ray diffractometry chart for a titanium oxide powder produced in Example 3.

FIG. 3 is an ESCA spectrometry chart for a titanium oxide powder produced in Example 1.

FIG. 4 is an ESCA spectrometry chart for a titanium oxide powder produced in Example 5.

FIG. 5 is an ESCA spectrometry chart for a titanium oxide powder produced in Comparative Example 1.

FIG. 6 is an ESCA spectrometry chart for a titanium oxide powder produced in Comparative Example 3.

FIG. 7 is transmission electron microscope (TEM) image for a titanium oxide powder produced in Example 1.

FIG. 8 is an absorbance graph for titanium oxide powders produced in Example 1, Comparative Example 1 and Comparative Example 8.

MODES FOR CARRYING OUT THE INVENTION

A titanium oxide powder of the present invention is doped with bivalent sulfur atoms ($S^{2-}$) and a ratio ($I_A/I_R$) of a peak intensity ($I_A$) of anatase-type crystals to a peak intensity ($I_R$) of rutile-type crystals as measured by X-ray diffractometry is 0.1 or less. We could produce for the first time such a titanium oxide powder by intense investigation. There will be detailed below.

In the titanium oxide powder of the present invention, a ratio ($I_A/I_R$) of a peak intensity ($I_A$) of anatase-type crystals to a peak intensity ($I_R$) of rutile-type crystals as measured by X-ray diffractometry is 0.1 or less. If a content of anatase-type crystals is high, photocatalytic activity is high, so that when the powder is used for an application in which the powder is exposed to ultraviolet light or visible light, an organic substance in contact with titanium oxide particles is likely to be deteriorated. In particular, when titanium oxide is added to a cosmetic, it is not desirable because it easily irritates the skin, leading to troubles.

Here, a peak intensity ($I_R$) of the rutile-type crystal is a peak intensity ($I_R$) of the rutile-type titanium oxide (110 plane) in the vicinity of $2\theta=27.5°$ in X-ray diffractometry. A peak intensity ($I_A$) of the anatase-type crystal is a peak intensity ($I_A$) of the anatase-type titanium oxide (101 plane) in the vicinity of $2\theta=25.3°$. These peak intensities can be obtained using the X-ray diffractometer described in Examples in the present specification or an equivalent device thereof under the measurement conditions described in Examples in the present specification or the equivalent measuring conditions. Each peak appearing in the X-ray diffractometry chart does not have to be an independent peak, and an anatase-type crystal peak may be observed as a shoulder peak of the rutile-type crystal peak. The peaks are separated by the analysis software attached to the device, and an intensity of each peak is calculated.

A ratio ($I_A/I_R$) is preferably 0.05 or less, and more preferably no peaks of anatase-type crystals are observed in X-ray diffractometry. Herein, "no peaks of anatase-type crystals are observed" means that no peaks of the anatase-type crystals are detected in measurement under the conditions described in Examples in the present application. Under the conditions of Examples, a ratio ($I_A/I_R$) is less than 0.03.

A major feature of the titanium oxide powder of the present invention is that it is doped with bivalent sulfur atoms ($S^{2-}$). A valence of sulfur doped in titanium dioxide ($TiO_2$) is described in Non-patent Reference Nos. 1 and 2. These documents suppose that in case of $S^{2-}$ doping, oxygen atoms (O) are replaced with sulfur atoms(S) in a titanium dioxide ($TiO_2$) crystal. In case of doping with tetravalent sulfur atoms ($S^{4+}$), it is supposed that titanium atoms (Ti) are replaced with sulfur atoms(S) in a titanium dioxide crystal. There may be hexavalent sulfur atoms ($S^{6+}$) near the surface of titanium dioxide particles. A valence of a sulfur atom can be determined by ESCA (Electron Spectroscopy for Chemical Analysis) spectrometry. Specifically, a peak of a binding energy of a bivalent sulfur atom ($S^{2-}$) in the 2p orbital is observed near 161 eV, while a peak of a binding energy of the 2p orbitals of $S^{4+}$ and $S^{6+}$ is observed at 167 to 168 eV.

Doping with bivalent sulfur atoms ($S^{2-}$) is confirmed by a peak observed near a binding energy of 161 eV in ESCA spectrometry. Specifically, it is sufficient that a peak near a binding energy of 161 eV is clearly observed in the spectrometry under the same conditions as in Examples of the present specification. In the titanium oxide powder of the present invention, a peak derived from $S^{2-}$ is observed inside the titanium oxide particles after etching the surface of the particles. As shown in FIGS. 3 and 4, the titanium oxide powder of the present invention often contains $S^{4+}$ and $S^{6+}$ in the surface and $S^{2-}$ in the inside. The reason for this is not clear, but it is possible that bivalent sulfur atoms ($S^{2-}$) are oxidized to $S^{4+}$ or $S^{6+}$ in the outermost surface.

Doping with bivalent sulfur atoms ($S^{2-}$) allows the titanium oxide to absorb light with a longer wavelength than undoped titanium oxide, and to absorb not only ultraviolet light but also blue visible light. Thus, the titanium oxide powder of the present invention exhibits yellow color.

When a cosmetic for shielding against ultraviolet rays contains titanium oxide fine particles having a size smaller than the wavelength of visible light, whitishness derived from titanium oxide is reduced, resulting in excellent transparency in use. However, since the particles are small, Rayleigh scattering occurs and blue light is scattered, leading to a problem that bluish color is felt when the cosmetic is applied to the skin. In contrast, since the titanium oxide powder of the present invention exhibits yellow color, it can negate blue color, providing a cosmetic having good color tone and excellent transparency. This color tone is also useful for paints, inks, toners, and so on other than cosmetics.

It is preferable that the titanium oxide powder of the present invention has an $L^*$ value of 94 to 99, an $a^*$ value of -2 to 1 and a $b^*$ value of 2 to 10 in an $L^*a^*b^*$ color scale. With an $L^*$ value being 94 or more, a powder exhibiting high whiteness without dullness can be obtained. An $L^*$ value is more preferably 95 or more, further preferably 96 or more, particularly preferably 97 or more. With an $a^*$ value being 1 or less, redness is suppressed. An $a^*$ value is more preferably 0 or less. Further, with a $b^*$ value being 2 or more, bluish tint can be effectively negated. A $b^*$ value is more preferably 3 or more, further preferably 4 or more. If a $b^*$ value is more than 10, yellow color may be too dark. A $b^*$ value is more preferably 8 or less, further preferably 6 or less.

A sulfur content of the titanium oxide powder of the present invention is preferably 500 to 6000 ppm. This sulfur content (ppm) is a mass of sulfur element based on a mass of the powder, and includes sulfur atoms of all valences such as $S^{2-}$, $S^{4+}$, and $S^{6+}$. When the sulfur content is 500 ppm or more, bluish tint can be effectively negated. The sulfur content is more preferably 1000 ppm or more, further preferably 1500 ppm or more. Meanwhile, the sulfur content is more preferably 5000 ppm or less.

It is preferable that an iron content of the titanium oxide powder of the present invention is 300 ppm or less. This iron content (ppm) is a mass of iron element based on a mass of the powder. When the iron content is 300 ppm or less, a dispersion, particularly a cosmetic exhibiting excellent transparency without dullness can be obtained. The iron content is more preferably 200 ppm or less, further preferably 150 ppm or less. If the iron content is excessively high, the titanium oxide particles may aggregate and transparency may be deteriorated.

It is preferable that the titanium oxide particles of the present invention have an average short-axis length of 4 to 13 nm and an average aspect ratio of 2 to 7. Here, the average aspect ratio is a value determined by (average long-axis length/average short-axis length). An average short-axis length (nm) and an average aspect ratio can be determined by taking a TEM photograph and counting 200 or more particles. When the average short-axis length is 13 nm or less, whitishness is reduced, and a dispersion, particularly a cosmetic exhibiting excellent transparency can be obtained. The average short-axis length is more preferably 12 nm or less, further preferably 11 nm or less. Meanwhile, it is difficult to synthesize titanium oxide particles having an average short-axis length of 4 nm or less, and thus, it is more preferably 5 nm or more.

A specific surface area of the titanium oxide powder of the present invention is preferably 110 to 300 $m^2/g$. When the specific surface area is 110 $m^2/g$ or more, whitishness is reduced and a dispersion, particularly a cosmetic exhibiting excellent transparency can be obtained. The specific surface area is more preferably 130 $m^2/g$ or more.

There will be described a method for producing the titanium oxide powder of the present invention. A suitable production method is a method for producing the titanium oxide powder, comprising an alkalization step of adding an alkali metal hydroxide to an aqueous dispersion of hydrous titanium oxide ($TiO_2 \cdot nH_2O$) to provide an alkali metal titanate, an acidification step of adding hydrochloric acid to an aqueous dispersion of the alkali metal titanate to provide titanium oxide ($TiO_2$) containing rutile-type crystals, and a drying step of drying the titanium oxide containing rutile-type crystals by heating, wherein, after the alkalization step and before the drying step, sulfurous acid, disulfurous acid, sulfuric acid or a salt thereof is added.

In the alkalizing step, an alkali metal hydroxide is added to an aqueous dispersion of hydrous titanium oxide (titanium dioxide hydrate: $TiO_2 \cdot nH_2O$) to provide an alkali metal titanate. There are no particular restrictions to a method for producing hydrous titanium oxide; for example, those produced by heating an aqueous solution of titanyl sulfate ($TiOSO_4$) for hydrolysis can be used. The hydrous titanium oxide thus obtained usually contains anatase-type crystals.

Examples of the alkali metal hydroxide added to the aqueous dispersion of hydrous titanium oxide include sodium hydroxide, potassium hydroxide and lithium hydroxide, preferably sodium hydroxide and potassium hydroxide, particularly preferably sodium hydroxide. A mole number of the alkali metal hydroxide added is preferably 2 to 20 times a mole number of titanium element in the hydrous titanium oxide. A heating temperature is preferably 60 to 120° C. Thus, an aqueous dispersion of alkali metal titanate is obtained. Examples of the alkali metal titanate include sodium titanate ($Na_2O_7Ti_3$), potassium titanate, and lithium titanate.

In the acidification step after the alkalization step, hydrochloric acid is added to the aqueous dispersion of the alkali metal titanate to give titanium oxide ($TiO_2$) containing rutile-type crystals. By adding hydrochloric acid to acidify the aqueous dispersion, an aqueous dispersion in which titanium oxide particles containing rutile-type crystals are dispersed can be obtained. It is preferable to add hydrochloric acid before heating, and a suitable heating temperature is 50 to 105° C. The amount of hydrochloric acid is an amount enough to neutralize the excess alkali in the aqueous dispersion and to make the aqueous dispersion acidic.

In the drying step after the acidification step, the titanium oxide particles generated in the acidification step are heated to remove water and dried. A suitable drying temperature is 70 to 300° C.

The method for producing the titanium oxide powder of the present invention is particularly characterized in that after the alkalization step and before the drying step, sulfurous acid, disulfurous acid, sulfuric acid or a salt thereof is added. By adding such a sulfur-containing compound, a titanium oxide powder doped with bivalent sulfur atoms ($S^{2-}$) can be obtained. As shown in Comparative Examples of the present specification, addition of a sulfur-containing compound such as thiourea or methanesulfonic acid did not allow for providing a titanium oxide powder doped with bivalent sulfur atoms ($S^{2-}$). It is not clearly understood why the titanium oxide obtained is doped with bivalent sulfur atoms ($S^{2-}$) by adding sulfurous acid, disulfurous acid, sulfuric acid or a salt thereof. It is surprising that despite that sulfurous acid and disulfurous acid contain tetravalent sulfur atoms ($S^{4+}$) and sulfuric acid contains hexavalent sulfur atoms ($S^{6+}$), they are taken as bivalent sulfur atoms ($S^{2-}$) into the titanium oxide crystals.

The timing of adding the sulfur-containing compound to the slurry can be immediately after the alkalizing step and immediately before the drying step, or at any timing between them. We have confirmed that a titanium oxide powder doped with bivalent sulfur atoms ($S^{2-}$) can be obtained by adding the sulfur-containing compound at any of these timings. In particular, preferred is a method comprising adding the sulfur-containing compound after the alkalizing step and then adding hydrochloric acid for acidification, or a method comprising adding a part of hydrochloric acid, then adding the sulfur-containing compound in the acidifying step after the alkalizing step, and then adding the remaining hydrochloric acid.

A compound added is sulfurous acid, disulfurous acid, sulfuric acid or a salt thereof. Here, if sulfurous acid or sulfuric acid that does not form a salt is added to an aqueous dispersion containing particles of an alkali metal titanate, these may rapidly react to form anatase-type crystals. Therefore, adding it as a sulfite, a disulfite, or a sulfate is preferable. In the light of effectively suppressing bluish color of the dispersion, a sulfite or disulfite is preferable, and a sulfite is more preferable. Here, a cation species in the salt is preferably an alkali metal ion, more preferably sodium ion. Specific examples include sodium sulfite ($Na_2SO_3$), sodium disulfite ($Na_2S_2O_5$), and sodium sulfate ($Na_2SO_4$).

It is preferable that the amount of sulfurous acid, disulfurous acid, sulfuric acid or a salt thereof added is 0.005 to 0.1 in a mass ratio based on the amount of titanium oxide ($TiO_2$). Here, the amount of titanium oxide ($TiO_2$) is a mole number of titanium element in the slurry to which the sulfur-containing compound is added multiplied by a formula weight of $TiO_2$, based on the total amount of titanium element contained in the alkali metal titanate and titanium oxide. With the mass ratio being 0.005 or more, bluish color can be effectively negated. The mass ratio is more preferably 0.01 or more. If the mass ratio is more than 0.1, anatase-type crystals may be present. Thus, the mass ratio is more preferably 0.07 or less.

After the drying step, pulverizing can be, if necessary, conducted to give the titanium oxide powder of the present invention. The titanium oxide powder of the present invention can be used for various applications as it is, but preferably its surface is coated. That is, a preferred embodiment of the present invention is a titanium oxide powder wherein the surface of titanium oxide particles contained in the above powder is coated with an inorganic or organic compound layer.

An inorganic compound with which the titanium oxide particles are coated preferably contains at least one element selected from the group consisting of aluminum, magnesium, calcium, silicon, zinc, titanium, zirconium, iron, cerium and tin. By coating with a compound containing these elements, durability and dispersion stability of the titanium oxide particles can be improved. A particularly suitable compound is an aluminum compound, and coating with a form of aluminum hydroxide is preferable. It allows for improving dispersion stability and suppressing photocatalytic activity peculiar to titanium oxide. An example of a method for coating with aluminum hydroxide is a method comprising adding a salt such as aluminum chloride to a slurry containing titanium oxide particles and hydrolyzing the slurry to precipitate aluminum hydroxide on the surface of the titanium oxide particles. A preferable content of aluminum in the titanium oxide powder is 2 to 30 parts by mass based in terms of $Al_2O_3$ based on 100 parts by mass of $TiO_2$.

An organic compound with which the titanium oxide particles are coated can be at least one selected from the group consisting of a fatty acid or a salt thereof, a silicone compound, a coupling agent and a fluorine compound. Among these, preferred is a fatty acid or a salt thereof, which can make the surface of the titanium oxide particles lipophilic and allows for easily dispersing in an oil phase. In particular, when being used as a cosmetic, the cosmetic applied to the skin is tolerant to coming off due to sweat or rain, and its durability is improved. Here, the fatty acid used is preferably a higher fatty acid having 12 to 30 carbon atoms, and the salt thereof is preferably an aluminum salt. An exemplary method for coating with a fatty acid or a salt thereof is a method comprising adding a fatty acid salt of an alkali metal to a slurry containing titanium oxide particles, and then adding a strong acid such as sulfuric acid to precipitate the free fatty acid on the surface of the titanium oxide particles. A preferable content of the fatty acid or a salt thereof in the titanium oxide powder is 2 to 50 parts by mass based on 100 parts by mass of $TiO_2$. The content is the amount converted to the free fatty acid.

The layer of the inorganic compound coating the surface of the titanium oxide particles does not have to be a uniform layer, and can partially cover the surface. The same applies to the layer of the organic compound. The layer of the inorganic compound and the layer of the organic compound can be formed as separate layers, or one layer can contain both the inorganic compound and the organic compound. In a preferred embodiment, the surface of the titanium oxide particles is covered with a layer containing aluminum hydroxide and a higher fatty acid having 12 to 30 carbon atoms or an aluminum salt thereof.

A dispersion prepared by dispersing the titanium oxide powder of the present invention thus obtained in a dispersion medium is a preferred embodiment. Here, the dispersion medium can be water or an organic solvent, or alternatively a mixed solvent of water and an organic solvent or an emulsion formed from water and an organic solvent.

Suitable uses are cosmetics, paints, inks, toners, and so on, which contain the titanium oxide powder of the present invention.

Among these, a particularly suitable use is a cosmetic, which is preferably used as a cosmetic having ultraviolet shielding effect. A cosmetic of the present invention can contain inorganic pigments and/or organic pigments other than the titanium oxide powder of the present invention. Examples of inorganic pigments which can be used include titanium oxide, zinc oxide, red iron oxide, yellow iron oxide, black iron oxide, ultramarine, Prussian blue, cerium oxide, talc, white mica, synthetic mica, phlogopite, black mica, synthetic fluorine phlogopite, mica titanium, micaceous iron oxide, sericite, zeolite, kaolin, bentonite, clay, silicic acid, silicic anhydride, magnesium silicate, aluminum silicate, calcium silicate, barium sulfate, magnesium sulfate, calcium sulfate, calcium carbonate, magnesium carbonate, boron nitride, bismuth oxychloride, alumina, zirconium oxide, magnesium oxide, chromium oxide, calamine, carbon black, hydroxyapatite and composites thereof. Examples of organic pigments which can be used include a silicone powder, a polyurethane powder, a cellulose powder, a nylon powder, a silk powder, a polymethyl methacrylate (PMMA) powder, starch, a polyethylene powder, a polystyrene powder, a tar dye, a natural dye and composites thereof.

A cosmetic of the present invention can contain other ingredients depending on the purpose. For example, a pH adjuster, a humectant, a thickener, a surfactant, a dispersion stabilizer, a preservative, an antioxidant, a sequestering agent, an astringent, an anti-inflammatory agent, an ultraviolet absorber, a perfume and so on can be added as appropriate.

Examples of the form of the cosmetic of the present invention include an emulsion, a lotion, an oil, a cream, a paste and the like. Specific uses include sunscreen cosmetics; makeup cosmetics such as makeup bases, foundations, concealers, control colors, lipsticks, lip balms, eye shadows, eye liners, mascara, and cheek colors; skin care cosmetics; and hair care cosmetics.

When the titanium oxide powder of the present invention is used for a paint or ink, titanium oxide particles can be dispersed in a solution in which a base polymer is dissolved, or the titanium oxide particles can be dispersed in an aqueous emulsion in which base polymer particles are dispersed. In addition, additives usually added to a paint or ink can be blended, including pigments, matting agents, surfactants, dispersion stabilizers, leveling agents, thickeners, antioxidants, and ultraviolet absorbers. In addition, some paints containing fine particles of titanium oxide have so-called "flip-flop" effect that color tone varies depending on a viewing angle, and by using the titanium oxide of the present invention, a "flip-flop" coating film with less bluish color can be formed.

When the titanium oxide powder of the present invention is used as an external additive for a toner, it is used as a mixture with toner particles containing a pigment. By using the fine particle titanium oxide, it is possible to provide a toner exhibiting excellent stability of charging performance under various environments can be provided. Here, the toner can contain various additives which are usually added.

EXAMPLES

There will be more specifically described with reference to Examples. The analysis methods and evaluation methods in the examples are as follows.
(1) X-Ray Diffractometry A titanium oxide powder pressed flat against a sample holder with a glass plate was measured by an X-ray diffractometer (manufactured by Philips). The measurement conditions are as follows.

Diffractometer system: XPERT-PRO
Radiation source: CuKα
Scan size: 2θ=0.008°
Voltage: 45 kV
Current: 20 mA
Measurement range: 2θ=5 to 100°
Attached software for analysis: HighScore Plus A peak intensity ($I_R$) of rutile-type titanium oxide (110 plane) near 2θ=27.5° and a peak intensity ($I_A$) of anatase-type titanium oxide (101 plane) near 2θ=25.3° were measured and their ratio ($I_A/I_R$) was calculated. Here, the peak search function of the attached software was used to perform peak search under the following conditions. When the peak search is performed under these conditions, a ratio ($I_A/I_R$) at the detection limit of the peak of the anatase type crystal is 0.03. Therefore, a ratio ($I_A/I_R$) when the peak of the anatase type crystal is not detected is less than 0.03.

Minimum significance: 0.50
Minimum peak chip: 0.10°
Maximum peak chip: 1.00°
Peak base width: 2.00°
Method: Minimum value of a secondary differential
(2) Contents of Sulfur Element and Iron Element The contents were measured using a scanning fluorescent X-ray analyzer "ZSX Primus II" manufactured by Rigaku Corporation. The titanium oxide powder as a sample was press-molded to prepare a pellet, and the contents (ppm) of sulfur element and iron element of the measurement sample were measured by a fundamental parameter method (FP method).
(3) ESCA Measurement ESCA (Electron Spectroscopy for Chemical Analysis) measurement was performed using an X-ray photoelectron spectroscopic analyzer "ESCA3400" manufactured by Shimadzu Corporation. The sample powder was compacted into a thin film and then fixed with a carbon tape for measurement. A distribution of sulfur elements in the depth direction of the sample was measured by repeatedly etching the surface by argon sputtering for 15 seconds. It was corrected with a binding energy for C1s of 284.6 eV. A peak of a binding energy of 2p orbital of a bivalent sulfur atom ($S^{2-}$) appears near 161 eV. The measurement and etching conditions are as follows.
(Measurement Conditions)

X-ray source: Mg-Kα ray
Filament voltage-current: 12 kV-15 mA
Vacuum degree: less than $1.0 \times 10^{-6}$ Pa
Measurement range: 150-180 eV
Measurement step: 0.1 eV
Cumulative number: 30
(Argon Etching Conditions)

Filament voltage-current: 2 kV-20 mA
Ion source: Argon gas
Vacuum degree during argon etching: $1.0 \times 10^{-4}$ Pa
Etching time: 15 seconds/run
(4) Shape and Dimensions of Particles A long-axis length (nm) and a short-axis length (nm) of each particle were determined by taking a transmission electron microscope (TEM) image and performing image processing on the particles. An aspect ratio is a value obtained by (long-axis length/short-axis length). Two hundred or more particles were measured, and an average short-axis length (nm) and an average aspect ratio were determined.
(5) Specific Surface Area A specific surface area was measured by the BET method using a fully automatic specific surface area measuring device "Macsorb HM model-1208" manufactured by Mountech Co., Ltd. The measurement was carried out after degassing at 150° C. for 20 minutes in a nitrogen gas atmosphere.
(6) Color Measurement was performed using a color difference meter "CR-400" manufactured by Konica Minolta Co., Ltd.

A sample used was prepared by filling an aluminum ring with a titanium oxide powder and pressure-molding it using a press machine. After performing white calibration of the color difference meter, an L* value, an a* value, and a b* value in the L*a*b* color scale were measured.

(7) Absorbance

A titanium oxide powder was press-molded, and measured for an absorbance by a diffuse reflectance spectroscopy using a spectrophotometer "U-4100" manufactured by Hitachi, Ltd. The measurement conditions are as follows.

Scan speed: 300 nm/min
Sampling interval: 2 nm
Measurement wavelength: 250 to 700 nm (8) Bluish Color An emulsified preparation was applied to the skin of the forearm under sunlight, and bluish color was visually evaluated, varying a viewing angle. In particular, a part where the veins could be seen through blue was observed for bluish color. Fifteen panelists evaluated according to the following criteria and the most frequent evaluation was adopted.

A: From immediately after the application of the emulsified preparation, bluish color was not observed, and when spreading the preparation was spread, bluish color was not felt.

B: Immediately after the application of the emulsified preparation, bluish color was observed, but when it was spread, bluish color disappeared.

C: Immediately after the application of the emulsion preparation, bluish color was observed, and even when it was thoroughly spread, slight bluish color was felt.

D: From immediately after the application of the emulsified preparation, bluish color was observed, and even when it was thoroughly spread, clear bluish color was felt.

(9) Transparency

The emulsified preparation was applied to the skin of the forearm under sunlight, and transparency was visually evaluated, varying a viewing angle. Fifteen panelists evaluated according to the following criteria and the most frequent evaluation was adopted.

A: From immediately after the application of the emulsified preparation, transparency was observed, and when it was spread, it was felt transparent.

B: Immediately after applying the emulsified preparation, transparency was not observed, but when it was thoroughly spread, it was felt transparent.

C: Immediately after the application of the emulsified preparation, transparency was not observed, and even when it was thoroughly spread, it was felt slightly opaque.

D: From immediately after the application of the emulsified preparation, opacity was noticeable, and even when it was thoroughly spread, it was clearly opaque and did not fit the skin.

Example 1

An aqueous solution of titanyl sulfate ($TiOSO_4$) was heated to 100° C. and hydrolyzed to precipitate hydrous titanium oxide (titanium dioxide hydrate) ($TiO_2 \cdot nH_2O$), giving a slurry. The slurry was filtered to give a cake, which was then washed with water to obtain 35 kg (10 kg in terms of $TiO_2$) of a hydrous titanium oxide cake. The hydrous titanium oxide thus obtained contains anatase-type crystals. To this cake was added 70 kg of a 48% by mass aqueous solution of sodium hydroxide with stirring, and then the mixture was heated. The cake was stirred at a temperature ranging from 95 to 105° C. for 2 hours to obtain a slurry of sodium titanate ($Na_2O_7Ti_3$). A cake obtained by filtering the slurry was thoroughly washed with water to obtain a cake of sodium titanate. Water was added to the cake obtained to give a slurry (a) containing 170 g/L of sodium titanate in terms of $TiO_2$.

Sodium sulfite was added to the slurry (a) containing sodium titanate. The amount of sodium sulfite added was 22.2 g based on 1 kg of $TiO_2$. To the slurry was added 14.0 kg of 35% by mass hydrochloric acid, and heated, and the slurry was aged at a temperature ranging from 95 to 105° C. for 2 hours. After aging, the slurry was diluted with water to obtain a slurry containing 70 g/L of titanium oxide in terms of $TiO_2$. The titanium oxide thus obtained contains rutile-type crystals. This titanium oxide slurry was warmed to 80° C. and a pH was adjusted to 7.0 with aqueous ammonia, and then the slurry was aged for 30 minutes. After the aging was completed, the slurry was readjusted to pH 7.0 with aqueous ammonia or hydrochloric acid and then filtered and washed to give a titanium oxide cake. This cake was dried at 110° C. and then crushed by an impact type crusher to give a titanium oxide powder, which was then sieved through a 0.3 mm sieve.

Using the titanium oxide powder thus obtained, analysis and evaluation were performed in accordance with the above method. FIG. 1 shows a chart of X-ray diffractometry. No peaks of anatase-type crystals were detected, and a ratio ($I_A/I_R$) of a peak intensity ($I_A$) of anatase-type crystals to a peak intensity ($I_R$) of rutile-type crystals was less than 0.03. X-ray fluorescence analysis revealed that a sulfur element content (a mass of sulfur element based on the whole mass) was 1720 ppm, and an iron element content (a mass of iron element based on the whole mass) was less than 70 ppm.

FIG. 3 shows a chart of ESCA measurement. In observation before etching (Ar-0 seconds), peaks derived from $S^{4+}$ and $S^{6+}$ were observed at a binding energy of 167 to 168 eV, but no peaks derived from $S^2$-were observed. On the other hand, in observation after etching for 30 seconds and 60 seconds (Ar-30 seconds, Ar-60 seconds), peaks derived from $S^{2-}$ were observed near a binding energy of 161 eV, but no peaks derived from $S^{4+}$ or $S^{6+}$ were observed.

FIG. 7 shows a transmission electron microscope (TEM) image. An average short-axis length calculated by image processing based on the TEM photograph was 10.3 nm, and an average aspect ratio was 4.5. A specific surface area measured by a BET method was 149 $m^2/g$. An L* value measured by a color difference meter was 97.63, an a* value was −0.73, and a b* value was 4.43. Further, FIG. 8 shows a graph of an absorbance measured by a spectrophotometer together with an absorbance of the titanium oxide powder obtained in Comparative Example 1 and Comparative Example 8. An absorbance of the titanium oxide powder of this example has a peak at a longer wavelength than that of Comparative Example 1 to which sodium sulfite was not added, and exhibited bright yellow color, and unlike Comparative Example 8 to which iron oxide was added, absorption was not substantially observed near 500 nm.

To the slurry (a) containing sodium titanate was added sodium sulfite. The amount of sodium sulfite was 22.2 g based on 1 kg of $TiO_2$. To the slurry was added 14.0 kg of 35% by mass hydrochloric acid, and the mixture was heated, and aged at a temperature ranging from 95 to 105° C. for 2 hours. The aged slurry was diluted with water to give a 70 g/L titanium oxide slurry in terms of $TiO_2$. The titanium oxide obtained contains rutile-type crystals. This titanium oxide slurry was warmed to 85° C., and after adding an aqueous 10% by mass solution of polyaluminum chloride (PAC: $[Al_3(OH)_nCl_{6-n}]_m$), the slurry was aged for 10 minutes. The amount of PAC added was 13 parts by mass as $Al_2O_3$ based on 100 parts by mass of $TiO_2$. A pH was adjusted to 6.0 using a 48% aqueous solution of sodium hydroxide and after aging for 30 minutes, sodium stearate was added. The amount of sodium stearate added was 30 parts by mass based on 100 parts by mass of $TiO_2$. After adding sodium stearate and aging for 60 minutes, a pH was adjusted to 6.0 with 50% by mass sulfuric acid, and the slurry was aged another 30 minutes, filtered, and washed with water, to provide a cake of titanium oxide coated with a layer of aluminum hydroxide and stearic acid (or aluminum stearate). The cake was dried at 110° C., then crushed by an impact crusher, and then sieved through a 0.3 mm sieve, to provide a surface-coated titanium oxide powder. Titanium oxide particles in the powder obtained were coated with a layer of aluminum hydroxide and stearic acid (or aluminum stearate). The titanium oxide powder obtained had an L* value of 97.81, an a* value of –0.57, and a b* value of 3.69.

Using the surface-coated titanium oxide powder thus obtained, an emulsified preparation to be a cosmetic was prepared. In a 100 mL polypropylene cup was placed 32.9 g of a mixture of oil phase materials as shown below, and the mixture was stirred at 1400 rpm using a high-speed emulsifying/dispersing machine "T.K. Robomix" manufactured by Primix Corporation while 4.9 g of the titanium oxide powder was added. Subsequently, a stirring speed was increased to 3000 rpm, and the mixture was stirred for 10 minutes. Then, while continuing stirring, 32.2 g of a mixture of aqueous phase materials as shown below was added, and the mixture was stirred at 3000 rpm for 5 minutes to prepare an emulsified preparation.

(Oil Phase Materials)
- 25.9 g of Cyclopentasiloxane: "KF-995" manufactured by Shin-Etsu Chemical Co., Ltd.
- 3.5 g of Liquid paraffin: "Moresco White P-70" manufactured by MORESCO Co., Ltd.
- 3.5 g of PEG-9-Dimethicone: "KF-6019" manufactured by Shin-Etsu Chemical Co., Ltd.

(Aqueous Phase Materials)
- 22.4 g of Ion-exchanged water
- 9.8 g of 1,3-butylene glycol The emulsified preparation thus obtained was evaluated for bluish color and transparency as described above. As a result, bluish color was evaluated as A, and transparency was also evaluated as A. The results of the above analysis and evaluation are summarized in Tables 1 and 2.

Example 2

A titanium oxide powder was produced, analyzed and evaluated as described in Example 1 except that the amount of sodium sulfite added was 50 g based on 1 kg of $TiO_2$. The evaluation results are summarized in Tables 1 and 2.

Example 3

A titanium oxide powder was produced, analyzed and evaluated as described in Example 1 except that the amount of sodium sulfite added was 75 g based on 1 kg of $TiO_2$. The evaluation results are summarized in Tables 1 and 2. FIG. 2 shows a chart of X-ray diffractometry. A peak of the anatase-type crystal was detected on the shoulder of a peak of the rutile-type crystal, and a ratio ($I_A/I_R$) of a peak intensity ($I_A$) of the anatase-type crystal to a peak intensity ($I_R$) of the rutile-type crystal was 0.04.

Example 4

A titanium oxide powder was produced, analyzed and evaluated as described in Example 1 except that instead of sodium sulfite, 16.7 g of sodium disulfite ($Na_2S_2O_5$) was added to 1 kg of $TiO_2$. The evaluation results are summarized in Tables 1 and 2.

Example 5

A titanium oxide powder was produced, analyzed and evaluated as described in Example 1 except that instead of sodium sulfite, 25 g of sodium sulfate ($Na_2SO_4$) was added to 1 kg of $TiO_2$. The evaluation results are summarized in Tables 1 and 2. FIG. 4 shows a chart of ESCA measurement. In observation before etching (Ar-0 seconds), peaks derived from $S^{4+}$ and $S^{6+}$ were observed at a binding energy of 167 to 168 eV, but no peaks derived from $S^{2-}$ were observed. On the other hand, in observation after etching for 30 seconds and 60 seconds (Ar-30 seconds, Ar-60 seconds), peaks derived from $S^{2-}$ were observed near a binding energy of 161 eV, but no peaks derived from $S^{4+}$ or $S^{6+}$ were observed.

Comparative Example 1

A titanium oxide powder was produced, analyzed and evaluated as described in Example 1 except that sodium sulfite was not added. The evaluation results are summarized in Tables 1 and 2. FIG. 5 shows a chart of ESCA measurement. No peaks derived from $S^{2-}$, $S^{4+}$ or $S^{6+}$ were observed before and after etching. FIG. 8 shows a graph of an absorbance measured by a spectrophotometer together with absorbances obtained in Example 1 and Comparative Example 8. An absorption end was at a shorter wavelength than that in Example 1 where sodium sulfite was added. The powder exhibited white color.

Comparative Example 2

An aqueous solution of titanyl sulfate ($TiOSO_4$) was hydrolyzed by heating to 100° C., to precipitate hydrous titanium oxide (titanium dioxide hydrate) ($TiO_2$°$nH_2O$), giving a slurry. A cake obtained by filtering the slurry was washed with water to obtain 35 kg (10 kg in terms of $TiO_2$) of a hydrous titanium oxide cake. The hydrous titanium oxide obtained contains anatase-type crystals. To this cake, 30 kg of a 48% by mass aqueous solution of sodium hydroxide was added with stirring and then the mixture was heated and was stirred at a temperature ranging from 95 to 105° C. for 2 hours to obtain a slurry of sodium titanate ($Na_2O_7Ti_3$). A cake obtained by filtering the slurry was thoroughly washed with water to give a cake of sodium titanate. Water was added to this cake to give a slurry (b) containing 160 g/L of sodium titanate in terms of $TiO_2$.

A titanium oxide powder was produced, analyzed and evaluated as described in Comparative Example 1, except that a slurry (b) was prepared under the conditions for producing a slurry containing sodium titanate, and the amount of 35% by mass hydrochloric acid added to the slurry (b) was 8.0 kg. The evaluation results are summarized in Tables 1 and 2. From this comparative example, a titanium oxide powder having a larger particle size than that of Comparative Example 1 could be obtained.

Comparative Example 3

A titanium oxide powder was produced, analyzed and evaluated as described in Example 1 except that 25 g of thiourea (($NH_2$)$_2$CS) was added to 1 kg of $TiO_2$ instead of sodium sulfite. The evaluation results are summarized in Tables 1 and 2. FIG. 6 shows a chart of ESCA measurement. No peaks derived from $S^{2-}$, $S^{4+}$ or $S^{6+}$ were observed before and after etching.

Comparative Example 4

A titanium oxide powder was produced, analyzed and evaluated as described in Example 1 except that 100 g of a 70% by mass aqueous solution of methanesulfonic acid ($CH_3SO_3H$) was added instead of sodium sulfite. The amount of methanesulfonic acid added to 1 kg of $TiO_2$ is 70 g. The evaluation results are summarized in Tables 1 and 2.

Comparative Example 5

A titanium oxide powder was produced, analyzed and evaluated as described in Example 1 except that 25 g of sodium nitrate ($NaNO_3$) was added to 1 kg of $TiO_2$ instead of sodium sulfite. The evaluation results are summarized in Tables 1 and 2.

Comparative Example 6

A titanium oxide powder was produced, analyzed and evaluated as described in Example 1 except that 50 g of disodium hydrogen phosphate ($Na_2HPO_4$) was added to 1 kg of $TiO_2$ instead of sodium sulfite. The evaluation results are summarized in Tables 1 and 2.

Comparative Example 7

To the slurry (a) containing sodium titanate was added 14.0 kg of 35% by mass hydrochloric acid, and the mixture was heated and aged at a temperature ranging from 95 to 105° C. for 2 hours. The aged slurry was diluted with water to give a 70 g/L titanium oxide slurry in terms of $TiO_2$. The obtained titanium oxide contains rutile-type crystals. This titanium oxide slurry was warmed to 80° C., a pH was adjusted to 7.0 with aqueous ammonia, and then polyferric sulfate ($Fe_2(OH)_n(SO_4)_{(3-n)/2}$) was added. The amount of polyferric sulfate added was 1 g in terms of $Fe_2O_3$ based on 1 kg of $TiO_2$. This slurry was adjusted to pH 7.0 with aqueous ammonia or hydrochloric acid and then aged for 30 minutes, and again adjusted to pH 7.0 with aqueous ammonia or hydrochloric acid. This slurry was filtered to provide a titanium oxide cake. The cake was dried at 110° C., then crushed by an impact crusher, and then sieved through a 0.3 mm sieve to give a titanium oxide powder.

Further, 14.0 kg of 35% by mass hydrochloric acid was added to the slurry (a) containing sodium titanate, and the mixture was heated and aged at a temperature ranging from 95 to 105° C. for 2 hours. The aged slurry was diluted with water to give a 70 g/L titanium oxide slurry in terms of $TiO_2$. The obtained titanium oxide contains rutile-type crystals. This titanium oxide slurry was warmed to 85° C., a 10% by mass aqueous solution of polyaluminum chloride (PAC) was added, and then the slurry was aged for 10 minutes. The amount of PAC added was 13 parts by mass as $Al_2O_3$ based on 100 parts by mass of $TiO_2$. After adjusting the pH to 6.0 with a 48% aqueous sodium hydroxide solution, the mixture was aged for 30 minutes, and polyferric sulfate ($Fe_2(OH)_n(SO_4)_{(3-n)/2}$) was added. The amount of polyferric sulfate added was 1 g in terms of $Fe_2O_3$ based on 1 kg of $TiO_2$. A pH of this titanium oxide slurry was adjusted to 6.0 with a 48% aqueous sodium hydroxide solution, and then sodium stearate was added. The amount of sodium stearate added was 30 parts by mass based on 100 parts by mass of $TiO_2$. After adding sodium stearate and aging for 60 minutes, a pH was adjusted to 6.0 with 50% by mass sulfuric acid, and the slurry obtained by aging for another 30 minutes was filtered and washed with water, to give a cake of titanium oxide coated with a layer of aluminum hydroxide and stearic acid (or aluminum stearate). The cake was dried at 110° C., then crushed by an impact crusher, and then sieved through a 0.3 mm sieve to provide a surface-coated titanium oxide powder. Titanium oxide particles in the powder obtained were coated with a layer of aluminum hydroxide and stearic acid (or aluminum stearate).

A surface-uncoated titanium oxide powder and a surface-coated titanium oxide powder produced as described above were analyzed and evaluated as described in Example 1. The evaluation results are summarized in Tables 1 and 2.

Comparative Example 8

A titanium oxide powder was produced, analyzed and evaluated as described in Comparative Example 7 except that the amount of polyferric sulfate added was 2.5 g in terms of $Fe_2O_3$ based on 1 kg of $TiO_2$. The evaluation results are summarized in Tables 1 and 2. FIG. 8 shows a graph of an absorbance measured by a spectrophotometer together with absorbances obtained in Example 1 and Comparative Example 1. It also absorbed light near 500 nm, that is, a longer wavelength than that in Example 1 to which sodium sulfite was added, and exhibited a slightly reddish dark color tone.

Comparative Example 9

A titanium oxide powder was produced, analyzed and evaluated as described in Comparative Example 7 except that the amount of polyferric sulfate added was 5 g in terms of $Fe_2O_3$ based on 1 kg of $TiO_2$. The evaluation results are summarized in Tables 1 and 2.

TABLE 1

| | Additive | Amount (g/kg) | $I_A/I_R$ | S content (ppm) | Fe content (ppm) | ESCA $S^2$-peak | Average short-axis length (nm) | Average aspect ratio | Specific surface area (m²/g) |
|---|---|---|---|---|---|---|---|---|---|
| Example 1 | $Na_2SO_3$ | 22.2 | <0.03 [*2)] | 1720 | <70 | Present | 10.3 | 4.5 | 149 |
| Example 2 | $Na_2SO_3$ | 50 | <0.03 [*2)] | 3040 | <70 | Present | 8.3 | 5.4 | 162 |
| Example 3 | $Na_2SO_3$ | 75 | 0.04 | 4160 | <70 | Present | 8.7 | 5.5 | 175 |
| Example 4 | $Na_2S_2O_5$ | 16.7 | <0.03 [*2)] | 1920 | <70 | Present | 10.2 | 4.9 | 138 |
| Example 5 | $Na_2SO_4$ | 25 | <0.03 [*2)] | 4320 | <70 | Present | 6.0 | 3.5 | 218 |
| Comparative Example 1 | Absent | 0 | <0.03 [*2)] | 40 | <70 | Absent | 8.0 | 5.9 | 145 |

TABLE 1-continued

| | Additive | Amount (g/kg) | $I_A/I_R$ | S content (ppm) | Fe content (ppm) | ESCA $S^2$-peak | Average short-axis length (nm) | Average aspect ratio | Specific surface area (m²/g) |
|---|---|---|---|---|---|---|---|---|---|
| Comparative Example 2 | Absent | 0 | <0.03 *2) | 360 | <70 | Absent | 11.9 | 4.9 | 112 |
| Comparative Example 3 | $(NH_2)_2CS$ | 25 | <0.03 *2) | 160 | <70 | Absent | 9.9 | 5.7 | 134 |
| Comparative Example 4 | $CH_3SO_3H$ | 70 | <0.03 *2) | 1920 | <70 | Absent | 10.1 | 5.8 | 141 |
| Comparative Example 5 | $NaNO_3$ | 25 | <0.03 *2) | 200 | <70 | Absent | 10.4 | 5.9 | 127 |
| Comparative Example 6 | $Na_2HPO_4$ | 50 | <0.03 *2) | 120 | <70 | Absent | 9.6 | 6.0 | 152 |
| Comparative Example 7 | $Fe_2(OH)_n(SO_4)_{(3-n)/2}$ | 1 *1) | <0.03 *2) | 120 | 692 | Absent | 8.1 | 5.6 | 146 |
| Comparative Example 8 | $Fe_2(OH)_n(SO_4)_{(3-n)/2}$ | 2.5 *1) | <0.03 *2) | 160 | 1825 | Absent | 8.2 | 5.4 | 141 |
| Comparative Example 9 | $Fe_2(OH)_n(SO_4)_{(3-n)/2}$ | 5 *1) | <0.03 *2) | 200 | 3448 | Absent | 8.2 | 5.4 | 142 |

*1) as $Fe_2O_3$
*2) No anatase-type crystals were detected.

TABLE 2

| | Additive | Amount (g/kg) | No surface coating L*a*b* color scale | | | Surface coating L*a*b* color scale | | | Appearance when being applied to skin | |
|---|---|---|---|---|---|---|---|---|---|---|
| | | | L* | a* | b* | L* | a* | b* | Bluish | Transparency |
| Example 1 | $Na_2SO_3$ | 22.2 | 97.63 | −0.73 | 4.43 | 97.81 | −0.57 | 3.69 | A | A |
| Example 2 | $Na_2SO_3$ | 50 | 97.41 | −0.62 | 6.98 | 97.1 | −0.66 | 5.63 | A | A |
| Example 3 | $Na_2SO_3$ | 75 | 96.54 | −1.37 | 10.03 | 95.14 | −1.09 | 7.43 | A | B |
| Example 4 | $Na_2S_2O_5$ | 16.7 | 97.06 | −1.21 | 4.6 | 97.76 | −0.64 | 3.83 | A | A |
| Example 5 | $Na_2SO_4$ | 25 | 97.64 | −0.43 | 3.67 | 97.38 | −0.42 | 3.35 | B | A |
| Comparative Example 1 | None | 0 | 98.32 | −0.38 | 1.63 | 98.06 | −0.01 | 0.97 | C | C |
| Comparative Example 2 | None | 0 | 98.05 | −0.32 | 1.26 | 98.14 | 0.1 | 0.83 | D | D |
| Comparative Example 3 | $(NH_2)_2CS$ | 25 | 98.13 | −0.22 | 1.72 | 98.19 | −0.02 | 0.61 | C | C |
| Comparative Example 4 | $CH_3SO_3H$ | 70 | 98.03 | −0.43 | 1.83 | 98.13 | −0.17 | 0.92 | C | C |
| Comparative Example 5 | $NaNO_3$ | 25 | 98.14 | −0.36 | 1.36 | 98.01 | −0.12 | 0.91 | C | C |
| Comparative Example 6 | $Na_2HPO_4$ | 50 | 98.04 | −0.39 | 1.72 | 98.09 | −0.02 | 0.94 | D | D |
| Comparative Example 7 | $Fe_2(OH)_n(SO_4)_{(3-n)/2}$ | 1 *1) | 90.03 | 2.65 | 11.25 | 95.80 | 0.99 | 4.16 | C | C |
| Comparative Example 8 | $Fe_2(OH)_n(SO_4)_{(3-n)/2}$ | 2.5 *1) | 88.43 | 2.83 | 14.60 | 94.31 | 1.46 | 5.84 | C | C |
| Comparative Example 9 | $Fe_2(OH)_n(SO_4)_{(3-n)/2}$ | 5 *1) | 82.00 | 5.58 | 17.68 | 93.02 | 1.92 | 7.25 | B | C |

*1) as $Fe_2O_3$

The invention claimed is:

1. A titanium oxide powder, wherein the titanium oxide powder is doped with bivalent sulfur atoms ($S^2$), a ratio ($I_A/I_R$) of a peak intensity ($I_A$) of anatase-type crystals to a peak intensity ($I_R$) of rutile-type crystals as measured by X-ray diffractometry is 0.1 or less and a specific surface area is 110 to 300 m²/g.

2. The titanium oxide powder according to claim 1, wherein no peaks of anatase-type crystals are observed in the X-ray diffractometry.

3. The titanium oxide powder according to claim 1, wherein a sulfur content is 500 to 6000 ppm.

4. The titanium oxide powder according to claim 1, wherein particles contained in the powder have an average short-axis length of 4 to 13 nm and an average aspect ratio of 2 to 7.

5. The titanium oxide powder according to claim 1, wherein in an L*a*b* color scale, an L* value is 94 to 99, an a* value is −2 to 1, and a b* value is 2 to 10.

6. The titanium oxide powder according to claim 1, wherein the surface of particles contained in the powder is coated with an inorganic or organic compound layer.

7. The titanium oxide powder according to claim 6, wherein the surface of the particles is coated with an inorganic compound layer and the inorganic compound contains at least one element selected from the group consisting of aluminum, magnesium, calcium, silicon, zinc, titanium, zirconium, iron, cerium and tin.

8. The titanium oxide powder according to claim 6, wherein the surface of the particles is coated with an organic compound layer and the organic compound is at least one selected from the group consisting of a fatty acid or a salt thereof, a silicone compound, a coupling agent and a fluorine compound.

9. A dispersion wherein the titanium oxide powder according to claim 1 is dispersed in a dispersion medium.

10. A cosmetic comprising the titanium oxide powder according to claim 1.

11. A paint comprising the titanium oxide powder according to claim 1.

12. An ink comprising the titanium oxide powder according to claim 1.

13. A toner comprising, as an external additive, the titanium oxide powder according to claim 1.

14. A method for producing the titanium oxide powder according to claim 1 comprising:

an alkalization step of adding an alkali metal hydroxide to an aqueous dispersion of hydrous titanium oxide to provide an alkali metal titanate, an acidification step of adding hydrochloric acid to an aqueous dispersion of the alkali metal titanate to provide titanium oxide containing rutile-type crystals, and a drying step of drying the titanium oxide containing rutile-type crystals by heating;

wherein, after the alkalization step and before the drying step, sulfurous acid, disulfurous acid, sulfuric acid or a salt thereof is added.

15. The method for producing a titanium oxide powder according to claim 14, wherein the amount of sulfurous acid, disulfurous acid, sulfuric acid or a salt thereof added is 0.005 to 0.1 in a mass ratio based on the amount of titanium oxide ($TiO_2$).

16. A method for producing a titanium oxide powder comprising coating the titanium oxide powder obtained by the production method according to claim 14 with an inorganic or organic compound layer.

17. A titanium oxide powder, wherein the titanium oxide powder is doped with bivalent sulfur atoms ($S^{2-}$), a ratio ($I_A/I_R$) of a peak intensity ($I_A$) of anatase-type crystals to a peak intensity ($I_R$) of rutile-type crystals as measured by X-ray diffractometry is 0.1 or less and a sulfur content is 500 to 6000 ppm.

18. The titanium oxide powder according to claim 17, wherein no peaks of anatase-type crystals are observed in the X-ray diffractometry.

19. The titanium oxide powder according to claim 17, wherein particles contained in the powder have an average short-axis length of 4 to 13 nm and an average aspect ratio of 2 to 7.

20. The titanium oxide powder according to claim 17, wherein in an L*a*b* color scale, an L* value is 94 to 99, an a* value is −2 to 1, and a b* value is 2 to 10.

21. The titanium oxide powder according to claim 17, wherein the surface of particles contained in the powder is coated with an inorganic compound layer and the inorganic compound contains at least one element selected from the group consisting of aluminum, magnesium, calcium, silicon, zinc, titanium, zirconium, iron, cerium and tin.

22. The titanium oxide powder according to claim 17, wherein the surface of particles contained in the powder is coated with an organic compound layer and the organic compound is at least one selected from the group consisting of a fatty acid or a salt thereof, a silicone compound, a coupling agent and a fluorine compound.

23. A dispersion wherein the titanium oxide powder according to claim 17 is dispersed in a dispersion medium.

24. A cosmetic comprising the titanium oxide powder according to claim 17.

* * * * *